US011031630B2

(12) United States Patent
Zhang et al.

(10) Patent No.: US 11,031,630 B2
(45) Date of Patent: Jun. 8, 2021

(54) ELECTROLYTE AND ELECTROCHEMICAL DEVICE

(71) Applicant: NINGDE AMPEREX TECHNOLOGY LIMITED, Ningde (CN)

(72) Inventors: Shuirong Zhang, Ningde (CN); Wenqiang Li, Ningde (CN); Qian Wen, Ningde (CN); Chao Tang, Ningde (CN)

(73) Assignee: NINGDE AMPEREX TECHNOLOGY LIMITED, Ningde (CN)

(*) Notice: Subject to any disclaimer, the term of this patent is extended or adjusted under 35 U.S.C. 154(b) by 62 days.

(21) Appl. No.: 16/422,012

(22) Filed: May 24, 2019

(65) Prior Publication Data
US 2020/0243906 A1 Jul. 30, 2020

(30) Foreign Application Priority Data

Jan. 25, 2019 (CN) .......................... 201910073562.1

(51) Int. Cl.
| | | |
|---|---|---|
| *H01M 10/0567* | (2010.01) | |
| *H01M 10/0569* | (2010.01) | |
| *H01M 10/0525* | (2010.01) | |
| *C07C 255/05* | (2006.01) | |
| *C07C 255/04* | (2006.01) | |
| *C07C 255/09* | (2006.01) | |
| *H01M 10/42* | (2006.01) | |
| *C07D 239/62* | (2006.01) | |
| *C07D 239/66* | (2006.01) | |
| *C07F 7/04* | (2006.01) | |

(52) U.S. Cl.
CPC ....... *H01M 10/0567* (2013.01); *C07C 255/04* (2013.01); *C07C 255/05* (2013.01); *C07C 255/09* (2013.01); *C07D 239/62* (2013.01); *C07D 239/66* (2013.01); *C07F 7/04* (2013.01); *H01M 10/0525* (2013.01); *H01M 10/0569* (2013.01); *H01M 10/4235* (2013.01); *H01M 2300/0025* (2013.01)

(58) Field of Classification Search
CPC .... H01M 10/0567; C07F 7/04; C07D 239/62; C07D 239/66; C07C 255/04; C07C 255/05; C07C 255/09
See application file for complete search history.

(56) References Cited

U.S. PATENT DOCUMENTS

2018/0198157 A1* 7/2018 Yu .................. C07C 255/54
2020/0176817 A1* 6/2020 Dou ................. H01M 10/0525

FOREIGN PATENT DOCUMENTS

| CN | 103764628 A | 4/2014 | |
|---|---|---|---|
| CN | 103880821 A | 6/2014 | |
| CN | 104025353 A | 9/2014 | |
| CN | 104513396 A | 4/2015 | |
| CN | 104752769 A | 7/2015 | |
| CN | 105261788 A | 1/2016 | |
| CN | 105914402 A | 8/2016 | |
| CN | 106410279 A | 2/2017 | |
| CN | 104766995 B | 3/2017 | |
| CN | 106654370 A | 5/2017 | |
| CN | 106910886 A | 6/2017 | |
| CN | 107017432 A | 8/2017 | |
| CN | 107078338 A | 8/2017 | |
| CN | 107732304 A | 2/2018 | |
| CN | 108232300 A | 6/2018 | |
| CN | 109244529 A | 1/2019 | |
| DE | 102015008345 A1 | 12/2015 | |
| DE | 102016010958 A1 * | 3/2017 | ........ H01M 10/0569 |
| DE | 102017006464 A1 * | 1/2018 | ............... A47J 37/07 |
| DE | 102017007426 A1 * | 1/2018 | .......... H01M 10/054 |
| JP | 20094352 A | 1/2009 | |

OTHER PUBLICATIONS

Machine translation of 109244529 (no date).*
Machine translation of DE102017006264 (no date).*
Machine translation of DE102017007426 (no date).*
Machine translation of DE2016010958 (no date).*
Chinese First Office Action dated Apr. 20, 2020 in counterpart Chinese application 201910073562.1, 10 pages in Chinese.
Chinese Second Office Action dated Aug. 11, 2020 in counterpart Chinese application 201910073562.1, 11 pages in Chinese.
Chinese Third Office Action dated Dec. 22, 2020 in counterpart Chinese application 201910073562.1, 10 pages in Chinese.

* cited by examiner

*Primary Examiner* — Amanda C. Walke
(74) *Attorney, Agent, or Firm* — Juan Carlos A. Marquez; Marquez IP Law Office, PLLC

(57) ABSTRACT

The present application provides an electrolyte and an electrochemical device. The electrolyte according to the present application comprises a carboxylate, a barbituric acid compound and a nitrile compound. Adding a barbituric acid compound and a nitrile compound of particular structure to an electrolyte containing a carboxylate solvent can significantly improve the rate performance of an electrochemical device, and mitigate capacity loss after storage at room temperature, and cycle fading and gas generation at high-temperature of the electrochemical device.

14 Claims, No Drawings

ELECTROLYTE AND ELECTROCHEMICAL DEVICE

BACKGROUND

1. Technical Field

The present application relates to the technical field of energy storage technologies, and more particularly to an electrolyte and an electrochemical device containing the same.

2. Description of the Related Art

Lithium-ion batteries are widely used in wearable devices, smart phones, unmanned aerial vehicles, electric vehicles, and other fields due to the advantages such as high energy density, long cycle life, and having no memory effect. With the broadening of the application of lithium-ion batteries and the development of modern information technologies, lithium-ion batteries are required to have, in addition to the conventional performances, rapid charge-discharge performance. Therefore, how to meet the rapid charge-discharge requirement of lithium-ion batteries has become an urgent problem in the industry.

There are many factors that affect the rapid charge and discharge of lithium ion batteries. As an important part of lithium-ion batteries, the electrolyte has a critical impact on the rapid charge and discharge performance of the batteries. The ability to rapidly charge and discharge the battery can be effectively improved by improving the electrolyte.

SUMMARY

An embodiment of the present application provides an electrolyte and an electrochemical device containing the same, wherein the electrolyte comprises a carboxylate, a barbituric acid compound, and a nitrile compound. Adding a barbituric acid compound and a nitrile compound of a particular structure to an electrolyte containing a carboxylate solvent can significantly improve the rate performance of an electrochemical device, and mitigate capacity loss after storage at room temperature, and cycle fading and gas generation at high-temperature of the electrochemical device.

In an embodiment, the present application provides an electrolyte comprising a carboxylate, a barbituric acid compound, and a nitrile compound.

According to an embodiment of the present application, the carboxylate includes at least one of the compounds of Formula 1:

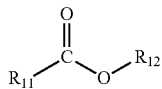

Formula 1 where $R_{11}$ and $R_{12}$ are each independently selected from $C_{1-12}$ alkyl or $C_{1-12}$ halogenated alkyl.

According to an embodiment of the present application, the carboxylate includes one or more of methyl acetate, ethyl acetate, propyl acetate, methyl propionate, ethyl propionate and propyl propionate.

According to an embodiment of the present application, the content of the carboxylate is about 5 wt % to about 70 wt % based on the total weight of the electrolyte.

According to an embodiment of the present application, the barbituric acid compound includes at least one of the compounds of Formula 2:

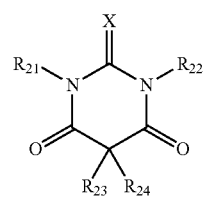

Formula 2 where $R_{21}$ and $R_{22}$ are each independently selected from hydrogen, $C_1$-$C_{12}$ alkyl, $C_1$-$C_{12}$ halogenated alkyl, $C_2$-$C_{12}$ alkenyl, $C_2$-$C_{12}$ halogenated alkenyl, $C_6$-$C_{26}$ aryl or $C_6$-$C_{26}$ halogenated aryl;

$R_{23}$ and $R_{24}$ are each independently selected from hydrogen, amino, $C_1$-$C_{12}$ alkyl, $C_1$-$C_{12}$ halogenated alkyl, $C_2$-$C_{12}$ alkenyl, $C_2$-$C_{12}$ halogenated alkenyl, $C_6$-$C_{26}$ aryl, $C_6$-$C_{26}$ halogenated aryl or —NH—R', in which R' is $C_1$-$C_{12}$ alkyl or $C_1$-$C_{12}$ halogenated alkyl; and X is selected from O or S.

According to an embodiment of the present application, the barbituric acid compound includes one or more of:

Compound 1-1

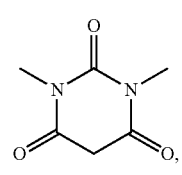

Compound 1-2

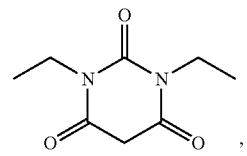

Compound 1-3

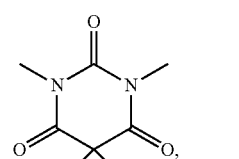

Compound 1-4

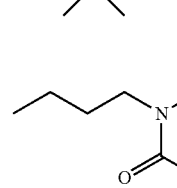

Compound 1-5

-continued

Compound 1-6

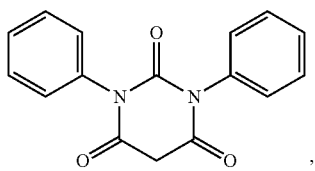

Compound 1-7

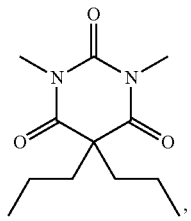

Compound 1-8

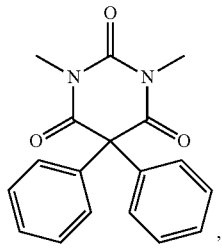

Compound 1-9

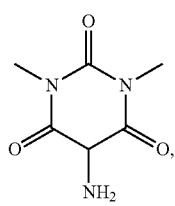

Compound 1-10

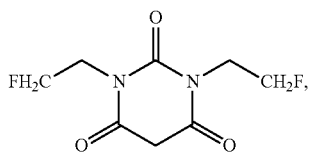

Compound 1-11

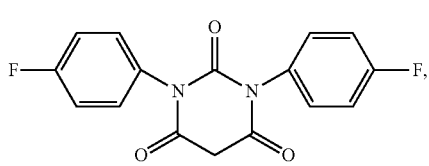

Compound 1-12

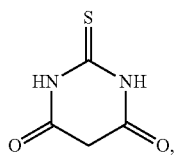

Compound 1-13

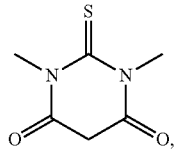

Compound 1-14

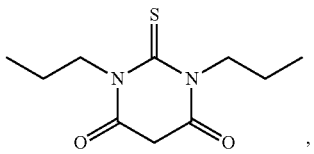

Compound 1-15

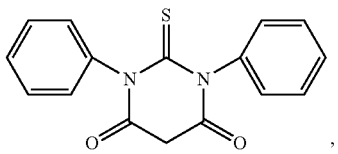

Compound 1-16

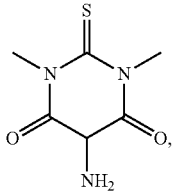

Compound 1-17

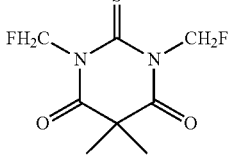

and

Compound 1-18

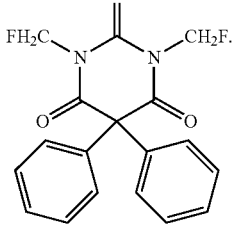

According to an embodiment of the present application, the content of the barbituric acid compound is about 0.01 wt % to about 5 wt % based on the total weight of the electrolyte.

According to an embodiment of the present application, the nitrile compound includes one or more of:

$$NC-R_{31}-CN \quad \text{Formula 3}$$

$$NC-R_{41}-\underset{H}{C}=\underset{H}{C}-R_{42}-NC \quad \text{and} \quad \text{Formula 4}$$

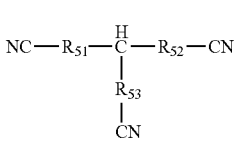

Formula 5 where $R_{31}$ is selected from $C_1$-$C_{12}$ alkylene or $C_1$-$C_{12}$ alkyleneoxy;

$R_{41}$, and $R_{42}$ are each independently selected from a bond or $C_1$-$C_{12}$ alkylene; and $R_{51}$, $R_{52}$, and $R_{53}$ are each independently selected from a bond, $C_1$-$C_{12}$ alkylene or $C_1$-$C_{12}$ alkyleneoxy.

According to an embodiment of the present application, the nitrile compound includes one or more of:

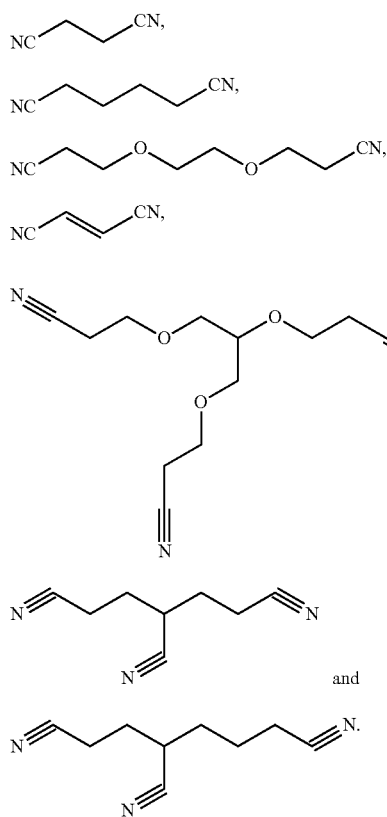

Compound 2-1
Compound 2-2
Compound 2-3
Compound 2-4
Compound 2-5
Compound 2-6
and
Compound 2-7

According to an embodiment of the present application, the content of the nitrile compound is about 0.5 wt % to about 12 wt % based on the total weight of the electrolyte.

According to an embodiment of the present application, the electrolyte further comprises a carbonate compound containing a silicon functional group.

According to an embodiment of the present application, the carbonate compound containing a silicon functional group includes at least one of the compounds of Formula 6:

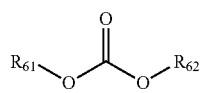

Formula 6 where $R_{61}$ and $R_{62}$ are each independently selected from $R^a$, $Si-(R^b)_3$ or $R^c-Si-(R^d)_3$, and at least one of $R_{61}$ and $R_{62}$ contains Si, in which $R^c$ is selected from $C_1$-$C_{12}$ alkylene, $C_2$-$C_{12}$ alkenylene, $C_6$-$C_{10}$ cyclohydrocarbylene or $C_6$-$C_{26}$ arylene group; and $R^a$, $R^b$, and $R^d$ are each independently selected from H, $C_1$-$C_{12}$ alkyl, $C_2$-$C_{12}$ alkenyl, $C_6$-$C_{10}$ cyclohydrocarbyl or $C_6$-$C_{26}$ aryl, and $R_{61}$ and $R_{62}$ are each independently substituted or unsubstituted, where when substituted, the substituent is halogen.

According to an embodiment of the present application, the carbonate compound containing a silicon-functional group includes one or more of:

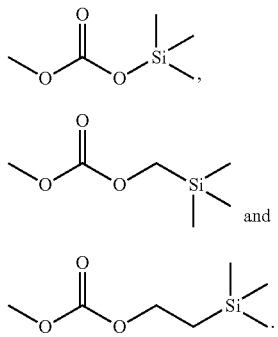

Compound 3-1
Compound 3-2
and
Compound 3-3

According to an embodiment of the present application, the content of the carbonate compound containing a silicon functional group is about 1 wt % to about 30 wt % based on the total weight of the electrolyte.

In another embodiment, the present application provides an electrochemical device comprising electrode and an electrolyte which is any electrolyte described above.

In another embodiment, the present application provides an electronic device including the electrochemical device.

Additional aspects and advantages of the embodiments of the present application will be partially described, illustrated or explained by way of examples in the description which follows.

DETAILED DESCRIPTION

Embodiments of the present application will be described in detail below. The embodiments of the present application should not be construed as limiting the present application. Unless otherwise expressly indicated, the following terms used herein have the meanings indicated below.

As used herein, the term "about" is used to describe and depict minor variations. When used in connection with an event or circumstance, the term may refer to an example in which the event or circumstance occurs precisely, and an example in which the event or circumstance occurs approximately. For example, when used in connection with a value, the term may refer to a range of variation less than or equal to ±10% of the stated value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. In addition, amounts, ratios, and other values are sometimes presented in a range format in this application.

It is to be understood that such a range format is provided for the sake of convenience and simplicity, and should be understood flexibly to include not only the numerical values that are explicitly defined in the range, but also all the individual values or sub-ranges that are included in the range, as if each value and sub-range are explicitly specified.

In the detailed description and claims, a list of items connected by the term "one of" means any one of the listed items. For example, if items A and B are listed, the phrase "one of A and B" means only A or only B. In another example, if items A, B, and C are listed, then the phrase "one of A, B, and C" means only A; only B; or only C. Item A may include a single or multiple elements. Item B may include a single or multiple elements. Item C may include a single or multiple elements.

In the detailed description and claims, a list of items connected by the term "at least one of" means any combination of the listed items. For example, if items A and B are listed, the phrase "at least one of A and B" means only A; only B; or A and B. In another example, if items A, B, and C are listed, then the phrase "at least one of A, B, and C" means only A; only B; only C; A and B (excluding C); A and C (excluding B); B and C (excluding A); or A, B, and C. Item A may include a single or multiple elements. Item B may include a single or multiple elements. Item C may include a single or multiple elements.

As used herein, the term "hydrocarbyl group" covers alkyl, alkenyl, and alkynyl groups. For example, the hydrocarbyl group is intended to be a straight-chain hydrocarbon structure having 1 to 20 carbon atoms. The hydrocarbyl group is also intended to be a branched or cyclic hydrocarbon structure having 3 to 20 carbon atoms. When a hydrocarbyl group having a specific number of carbon atoms is defined, it is intended to cover all geometric isomers having the carbon number. The hydrocarbyl group herein may also be a hydrocarbyl group having 1 to 15 carbon atoms, a hydrocarbyl group having 1 to 10 carbon atoms, a hydrocarbyl group having 1 to 5 carbon atoms, a hydrocarbyl group having 5 to 20 carbon atoms, a hydrocarbyl group having 5 to 15 carbon atoms or a hydrocarbyl group having 5 to 10 carbon atoms. Additionally, the hydrocarbyl group can be optionally substituted. For example, the hydrocarbyl group may be substituted by halogen including fluorine, chlorine, bromine, and iodine, an alkyl group, an aryl group or a heteroaryl group.

As used herein, the term "cyclohydrocarbyl group" covers cyclic hydrocarbyl groups. For example, the cyclohydrocarbyl group may be a cyclohydrocarbyl group having 3-20 carbon atoms, a cyclohydrocarbyl group having 3-15 carbon atoms, a cyclohydrocarbyl group having 3-10 carbon atoms, a cyclohydrocarbyl group having 3-6 carbon atoms, a cyclohydrocarbyl group having 5-20 carbon atoms, a cyclohydrocarbyl group having 5-15 carbon atoms, or a cyclohydrocarbyl group having 5-10 carbon atoms. Additionally, the cyclohydrocarbyl group can be optionally substituted. For example, the cyclohydrocarbyl group may be substituted by halogen including fluorine, chlorine, bromine, and iodine, an alkyl group, an aryl group or a heteroaryl group.

As used herein, the term "cyclohydrocarbylene group" covers cyclic hydrocarbylene groups. For example, the cyclohydrocarbylene group may be a cyclohydrocarbylene group having 3-20 carbon atoms, a cyclohydrocarbylene group having 3-15 carbon atoms, a cyclohydrocarbylene group having 3-10 carbon atoms, a cyclohydrocarbylene group having 3-6 carbon atoms, a cyclohydrocarbylene group having 5-20 carbon atoms, a cyclohydrocarbylene group having 5-15 carbon atoms, or a cyclohydrocarbylene group having 5-10 carbon atoms. Additionally, the cyclohydrocarbylene group can be optionally substituted. For example, the cyclohydrocarbylene group may be substituted by halogen including fluorine, chlorine, bromine, and iodine, an alkyl group, an aryl group or a heteroaryl group.

As used herein, the term "alkyl group" is intended to be a linear saturated hydrocarbon structure having 1 to 20 carbon atoms. The alkyl group is also intended to be a branched or cyclic hydrocarbon structure having 3 to 20 carbon atoms. For example, the alkyl group may be an alkyl group having 1-20 carbon atoms, an alkyl group having 1-12 carbon atoms, an alkyl group having 1-5 carbon atoms, an alkyl group having 5-20 carbon atoms, an alkyl group having 5-15 carbon atoms, or an alkyl group having 5-10 carbon atoms. When an alkyl group having a specific number of carbon atoms is defined, it is intended to cover all geometric isomers having the carbon number. Therefore, for example, "butyl" means n-butyl, sec-butyl, isobutyl, tert-butyl and cyclobutyl; and "propyl" includes n-propyl, isopropyl and cyclopropyl. Examples of the alkyl group include, but are not limited to, methyl, ethyl, n-propyl, isopropyl, cyclopropyl, n-butyl, isobutyl, sec-butyl, tert-butyl, cyclobutyl, n-pentyl, isoamyl, neopentyl, cyclopentyl, methylcyclopentyl, ethylcyclopentyl, n-hexyl, isohexyl, cyclohexyl, n-heptyl, octyl, cyclopropyl, cyclobutyl, norbornanyl and so on. Additionally, the alkyl group can be optionally substituted.

As used herein, the term "cycloalkyl group" covers cyclic alkyl groups. The cycloalkyl group may be a cycloalkyl group having 3 to 20 carbon atoms, a cycloalkyl group having 6 to 20 carbon atoms, a cycloalkyl group having 3 to 12 carbon atoms, or a cycloalkyl group having 3 to 6 carbon atoms. For example, the cycloalkyl group may be cyclopropyl, cyclobutyl, cyclopentyl, cyclohexyl or the like. Additionally, the cycloalkyl group can be optionally substituted.

As used herein, the term "alkylene group" means a linear or branched divalent saturated hydrocarbyl group. For example, the alkylene group may be an alkylene group having 1-20 carbon atoms, an alkylene group having 1-15 carbon atoms, an alkylene group having 1-12 carbon atoms, an alkylene group having 1-5 carbon atoms, an alkylene group having 5-20 carbon atoms, an alkylene group having 5-15 carbon atoms, or an alkylene group having 5-10 carbon atoms. A representative alkylene group includes (for example) methylene, ethane-1,2-diyl ("ethylidene"), propane-1,2-diyl, propane-1,3-diyl, butane-1, 4-diyl, pentane-1,5-diyl and the like. Additionally, the alkylene group can be optionally substituted.

As used herein, the term "alkenyl group" refers to a monovalent unsaturated hydrocarbyl group which may be straight or branched and which has at least one and usually 1, 2 or 3 carbon-carbon double bonds. Unless otherwise defined, the alkenyl group typically contains from 2 to 20 carbon atoms, for example an alkenyl group having 2 to 20 carbon atoms, an alkenyl group having 6 to 20 carbon atoms, an alkenyl group having 2 to 12 carbon atoms or an alkenyl group having 2 to 6 carbon atoms. Representative alkenyl groups include (for example) ethenyl, n-propenyl, iso-propenyl, n-but-2-enyl, butyl-3-enyl, n-hex-3-enyl, and the like. Additionally, the alkenyl group can be optionally substituted.

As used herein, the term "alkenylene group" covers both linear and branched alkenylene groups. When an alkenylene group having a specific number of carbon atoms is defined, it is intended to cover all geometric isomers having the carbon number. For example, the alkenylene group may be an alkenylene group having 2-20 carbon atoms, an alkenylene group having 2-15 carbon atoms, an alkenylene group having 2-10 carbon atoms, an alkenylene group having 2-5 carbon atoms, an alkenylene group having 5-20 carbon atoms, an alkenylene group having 5-15 carbon atoms, or an alkenylene group having 5-10 carbon atoms. A representative alkenylene group includes (for example) ethenylene, propenylene, butenylene and the like. Additionally, the alkenylene group can be optionally substituted.

As used herein, the term "aryl" covers both monocyclic and polycyclic systems. A polycyclic ring may have two or more rings in which two carbons are shared by two adjacent rings (where the rings are "fused"), in which at least one of the rings is aromatic and other rings may be for example, a cycloalkyl group, a cycloalkenyl group, an aryl group, a heterocyclyl group and/or a heteroaryl group. For example, the aryl group may be $C_6$-$C_{50}$ aryl, $C_6$-$C_{40}$ aryl, $C_6$-$C_{30}$ aryl, $C_6$-$C_{26}$ aryl, $C_6$-$C_{20}$ aryl or $C_6$-$C_{10}$ aryl. A representative aryl group includes (for example) phenyl, methylphenyl, propylphenyl, isopropylphenyl, benzyl and naphthalen-1-yl, naphthalen-2-yl and the like. Additionally, the aryl group can be optionally substituted.

As used herein, the term "arylene" covers both monocyclic and polycyclic systems. A polycyclic ring may have two or more rings in which two carbons are shared by two adjacent rings (where the rings are "fused"), in which at least one of the rings is aromatic and other rings may be a cycloalkyl group, a cycloalkenyl group, an aryl group, a heterocyclyl group and/or a heteroaryl group. For example, the arylene group may be a $C_6$-$C_{50}$ arylene group, a $C_6$-$C_{40}$ arylene group, a $C_6$-$C_{30}$ arylene group, a $C_6$-$C_{20}$ arylene, or a $C_6$-$C_{10}$ arylene. Additionally, the arylene group can be optionally substituted.

As used herein, the term "alkyleneoxy" refers to a -L-O— group, wherein L is an alkylene group. For example, the alkyleneoxy group may be an alkyleneoxy group having 1-20 carbon atoms, an alkyleneoxy group having 1-12 carbon atoms, an alkyleneoxy group having 1-5 carbon atoms, an alkyleneoxy group having 5-20 carbon atoms, an alkyleneoxy group having 5-15 carbon atoms, or a alkyleneoxy group having 5-10 carbon atoms. Additionally, the alkyleneoxy group can be optionally substituted.

As used herein, the term "nitrile compound" refers to a compound containing a cyano (—CN) functional group.

As used herein, the term "barbituric acid compound" covers barbituric acid and its derivatives.

As used herein, the term "halogen" covers F, Cl, Br or I.

As used herein, the term "bond" covers a single bond, a carbon-carbon double bond or a carbon-carbon triple bond.

When the above substituents are substituted, the substituent is selected from the group consisting of halogen, an alkyl group, a cycloalkyl group, an alkenyl group, and an aryl group.

As used herein, the content of each component in the electrolyte is calculated based on the total weight of the electrolyte.

I. Electrolyte

An embodiment of the present application provides an electrolyte comprising a carboxylate, a barbituric acid compound, and a nitrile compound.

In some embodiments, the carboxylate is at least one selected from the compounds of Formula 1:

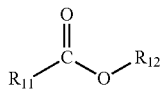

Formula 1 where $R_{11}$ and $R_{12}$ are each independently selected from $C_1$-$C_{20}$ alkyl, $C_1$-$C_{12}$ alkyl, $C_1$-$C_6$ alkyl, $C_1$-$C_{20}$ halogenated alkyl, $C_1$-$C_{12}$ halogenated alkyl or $C_1$-$C_6$ halogenated alkyl.

In some embodiments, the carboxylate is one or more selected from methyl acetate, ethyl acetate, propyl acetate, methyl propionate, ethyl propionate and propyl propionate.

In some embodiments, the content of the carboxylate is about 5 wt % to about 70 wt % based on the total weight of the electrolyte. In some embodiments, the content of the carboxylate is about 10 wt % to about 60 wt %. In some embodiments, the content of the carboxylate is about 20 wt % to about 50 wt %. In some embodiments, the content of the carboxylate is about 30 wt % to about 40 wt %. If the content of the carboxylate is about 5 wt % to about 70 wt %, the impedance reduction and the improvement of the rate performance of the battery are significant, and the irreversible side reaction decreases.

In some embodiments, the barbituric acid compound is at least one selected from the compounds of Formula 2:

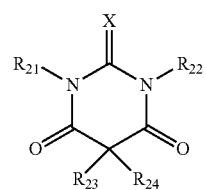

Formula 2 where $R_{21}$ and $R_{22}$ are each independently selected from hydrogen, $C_1$-$C_{20}$ alkyl, $C_1$-$C_{12}$ alkyl, $C_1$-$C_6$ alkyl, $C_1$-$C_{20}$ halogenated alkyl, $C_1$-$C_{12}$ halogenated alkyl, $C_1$-$C_6$ halogenated alkyl, $C_2$-$C_{20}$ alkenyl, $C_2$-$C_{12}$ alkenyl, $C_2$-$C_6$ alkenyl, $C_2$-$C_{20}$ halogenated alkenyl, $C_2$-$C_{12}$ halogenated alkenyl, $C_2$-$C_6$ halogenated alkenyl, $C_6$-$C_{50}$ aryl, $C_6$-$C_{26}$ aryl, $C_6$-$C_{12}$ aryl, $C_6$-$C_{50}$ halogenated aryl, $C_6$-$C_{26}$ halogenated aryl or $C_6$-$C_{12}$ halogenated aryl;

$R_{23}$ and $R_{24}$ are each independently selected from hydrogen, amino, $C_1$-$C_{20}$ alkyl, $C_1$-$C_{12}$ alkyl, $C_1$-$C_6$ alkyl, $C_1$-$C_{20}$ halogenated alkyl, $C_1$-$C_{12}$ halogenated alkyl, $C_1$-$C_6$ halogenated alkyl, $C_2$-$C_{20}$ alkenyl, $C_2$-$C_{12}$ alkenyl, $C_2$-$C_6$ alkenyl, $C_2$-$C_{20}$ halogenated alkenyl, $C_2$-$C_{12}$ halogenated alkenyl, $C_2$-$C_6$ halogenated alkenyl, $C_6$-$C_{50}$ aryl, $C_6$-$C_{26}$ aryl, $C_6$-$C_{12}$ aryl, $C_6$-$C_{50}$ halogenated aryl, $C_6$-$C_{26}$ halogenated aryl or $C_6$-$C_{12}$ halogenated aryl, or —NH—R', in which R' is $C_1$-$C_{20}$ alkyl, $C_1$-$C_{12}$ alkyl, $C_1$-$C_6$ alkyl, $C_1$-$C_{20}$ halogenated alkyl, $C_1$-$C_{12}$ halogenated alkyl or $C_1$-$C_6$ halogenated alkyl; and X is selected from O or S.

In some embodiments, the barbituric acid compound is one or more selected from:

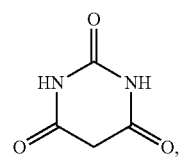

Compound 1-1

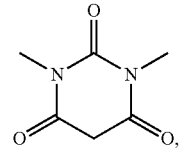

Compound 1-2

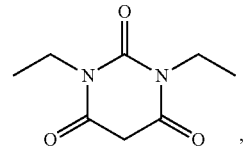

Compound 1-3

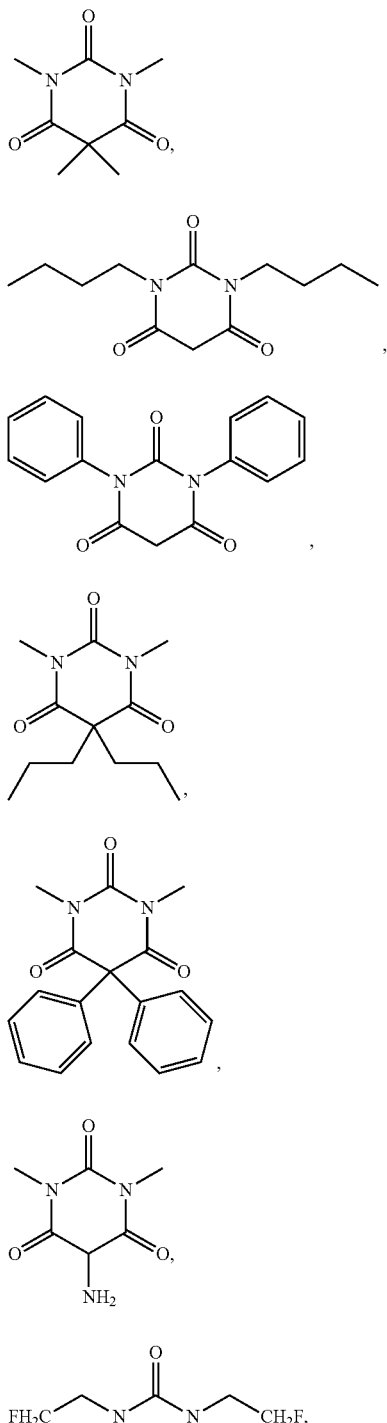

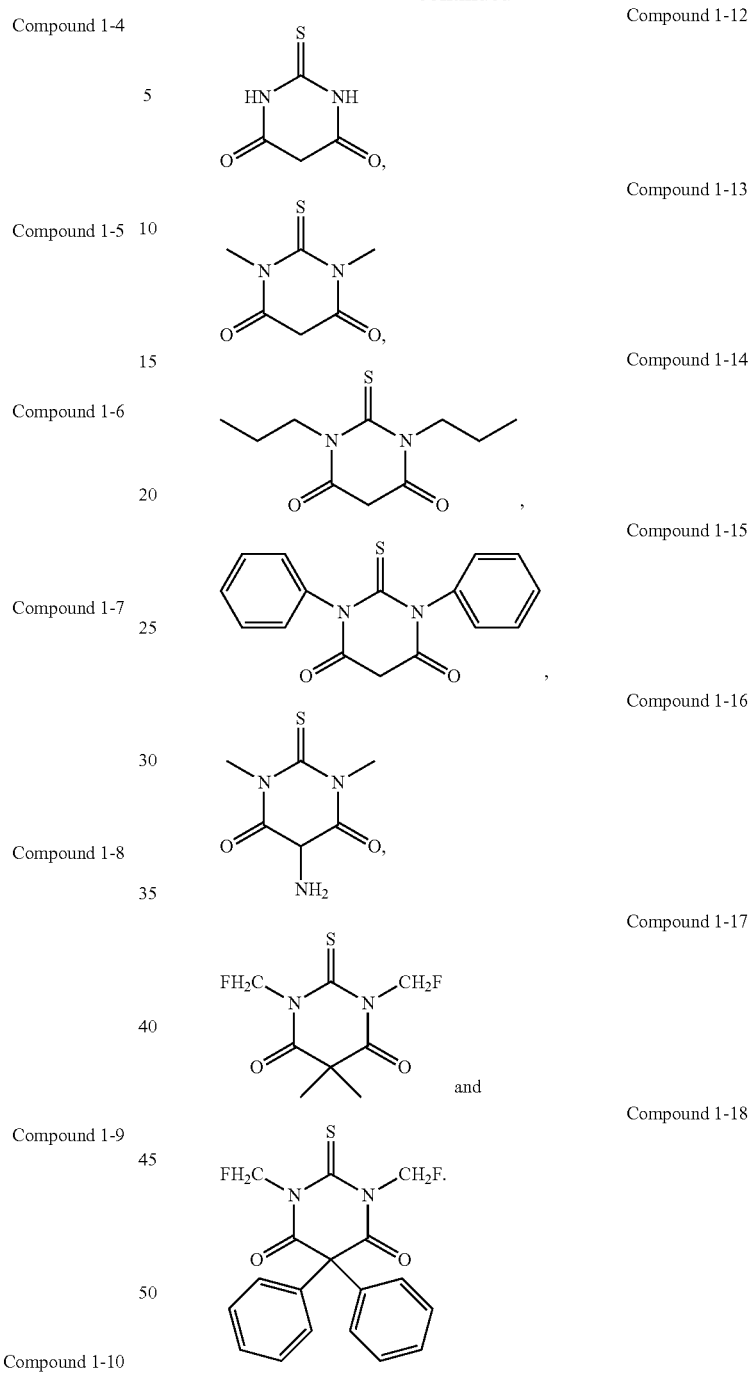

In some embodiments, the content of the barbituric acid compound is about 0.01 wt % to about 5 wt % based on the total weight of the electrolyte. In some embodiments, the content of the barbituric acid compound is about 0.01 wt % to about 4 wt %. In some embodiments, the content of the barbituric acid compound is about 0.01 wt % to about 3 wt %. In some embodiments, the content of the barbituric acid compound is about 0.01 wt % to about 2 wt %. In some embodiments, the content of the barbituric acid compound is about 0.05 wt % to about 5 wt %. In some embodiments, the content of the barbituric acid compound is about 1 wt % to about 3 wt %. When the content of the barbituric acid compound is about 0.01 wt % to about 5 wt %, an intact and effective cathode electrolyte interface (CEI) film can be formed on the surface of the cathode, thereby effectively preventing the side reaction caused by an electron transfer between the electrolyte and the electrode.

In some embodiments, the nitrile compound is one or more selected from:

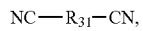

Formula 3

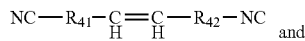
and

Formula 4

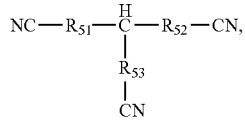

Formula 5 wherein, $R_{31}$ is selected from $C_1$-$C_{20}$ alkylene, $C_1$-$C_{12}$ alkylene, $C_1$-$C_6$ alkylene, $C_1$-$C_{20}$ alkyleneoxy, $C_1$-$C_{12}$alkyleneoxy or $C_1$-$C_6$ alkyleneoxy;

$R_{41}$, and $R_{42}$ are each independently selected from a bond, $C_1$-$C_{20}$ alkylene, $C_1$-$C_{12}$ alkylene or $C_1$-$C_6$ alkylene group; and $R_{51}$, $R_{52}$, and $R_{53}$ are each independently selected from a bond, $C_1$-$C_{20}$ alkylene, $C_1$-$C_{12}$ alkylene, $C_1$-$C_6$ alkylene, $C_1$-$C_{20}$ alkyleneoxy, $C_1$-$C_{12}$ alkyleneoxy or $C_1$-$C_6$ alkyleneoxy.

In some embodiments, the nitrile compound is one or more selected from:

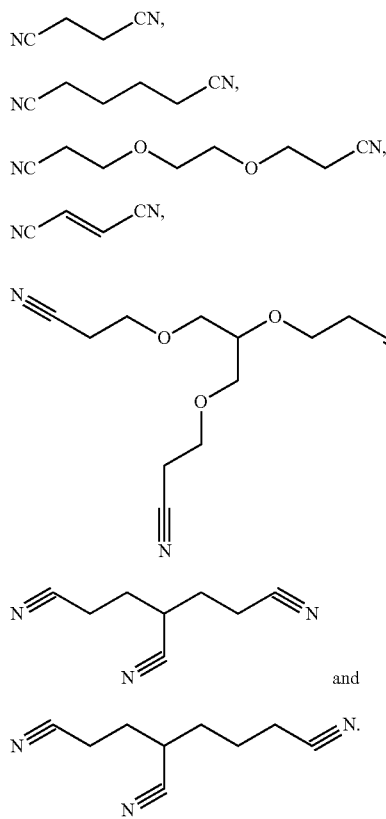

Compound 2-1

Compound 2-2

Compound 2-3

Compound 2-4

Compound 2-5

Compound 2-6 and

Compound 2-7

In some embodiments, the content of the nitrile compound is about 0.5 wt % to about 12 wt % based on the total weight of the electrolyte. In some embodiments, the content of the nitrile compound is about 0.5 wt % to about 10 wt %. In some embodiments, the content of the nitrile compound is about 0.5 wt % to about 5 wt %. In some embodiments, the content of the nitrile compound is about 2 wt % to about 5 wt %. In some embodiments, the content of the nitrile compound is about 2 wt % to about 10 wt %. In some embodiments, the content of the nitrile compound is about 3 wt % to about 10 wt %. When the content of the nitrile compound in the electrolyte is about 0.5 wt % to about 12 wt %, it has a significant isolation effect on the components susceptible to oxidization on the surface of the cathode and in the electrolyte, thereby significantly improving the cycle performance and high-temperature storage performance of lithium ion batteries.

In some embodiments, the electrolyte further comprises a carbonate compound containing a silicon functional group. The carbonate compound containing a silicon functional group works in combination with the carboxylate, barbituric acid compound, and nitrile compound, such that the electrolyte has excellent chemical stability, thermal stability, and oxidation resistance, and low surface tension; and can form a stable protection film on the surface of the electrode, thereby alleviating the capacity loss after storage at room temperature and the heat generation resulting from decomposition of the electrolyte on the surface of the electrode during the overcharge process of the lithium ion battery, so as to improve the overcharge performance of the lithium ion battery.

In some embodiments, the carbonate compound containing a silicon functional group is at least one selected from the compounds of Formula 6:

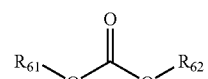

Formula 6 where $R_{61}$ and $R_{62}$ are each independently selected from $R^a$, Si—$(R^b)_3$ or $R^c$—Si—$(R^d)_3$, and at least one of $R_{61}$ and $R_{62}$ contains Si, in which $R^c$ is selected from $C_1$-$C_{12}$ alkylene, $C_2$-$C_{12}$ alkenylene, $C_6$-$C_{10}$ cyclohydrocarbylene or $C_6$-$C_{26}$ arylene; and $R^a$, $R^b$, and $R^d$ are each independently selected from H, $C_1$-$C_{20}$ alkyl, $C_1$-$C_{12}$ alkyl, $C_1$-$C_6$ alkyl, $C_2$-$C_{20}$ alkenyl, $C_2$-$C_{12}$ alkenyl, $C_2$-$C_6$ alkenyl, $C_6$-$C_{20}$ cyclohydrocarbyl, $C_6$-$C_{10}$ cyclohydrocarbyl, $C_6$-$C_{50}$ aryl, $C_6$-$C_{26}$ aryl, and $C_6$-$C_{12}$ aryl, and $R_{61}$ and $R_{62}$ are each independently substituted or unsubstituted, wherein when substituted, the substituent is halogen.

In some embodiments, the carbonate compound containing a silicon functional group is one or more selected from:

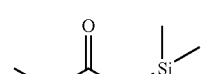

Compound 3-1

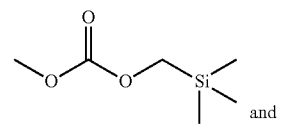

Compound 3-2 and

-continued

Compound 3-3

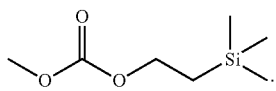

In some embodiments, the content of the carbonate compound containing a silicon functional group is about 1 wt % to about −30 wt % based on the total weight of the electrolyte. In some embodiments, the content of the carbonate compound containing a silicon functional group is about 1 wt % to about 20 wt %. In some embodiments, the content of the carbonate compound containing a silicon functional group is about 1 wt % to about 15 wt %. In some embodiments, the content of the carbonate compound containing a silicon functional group is about 1 wt % to about 10 wt %. In some embodiments, the content of the carbonate compound containing a silicon functional group is about 5 wt % to about 20 wt %. In some embodiments, the content of the carbonate compound containing a silicon functional group is about 10 wt % to about 20 wt %.

In some embodiments, the electrolyte comprises a lithium salt which is one or more selected from an inorganic lithium salt and an organic lithium salt. In some embodiments, the lithium salt is one or more selected from lithium hexafluorophosphate ($LiPF_6$), lithium difluorophosphate ($LiPO_2F_2$), lithium tetrafluoroborate ($LiBF_4$), lithium hexafluoroarsonate, lithium perchlorate, lithium bis(fluorosulphonyl)imide (LiFSI), lithium bis(trifluoromethanesulphonyl)imide (LiTFSI), lithium bis(oxalato)borate ($LiB(C_2O_4)_2$, LiBOB) and lithium difluoro(oxalato)borate ($LiBF_2(C_2O_4)$, LiDFOB).

In some embodiments, the concentration of the lithium salt is about 0.5 M to about 1.5 M. In some embodiments, the concentration of the lithium salt is about 0.8 M to about 1.3 M. In some embodiments, the concentration of the lithium salt is about 0.5 M to about 1.2 M.

In some embodiments, the electrolyte further comprises a carbonate compound. The carbonate may be any kind of carbonate as long as it can be used as an organic solvent for a nonaqueous electrolyte.

In some embodiments, the carbonate is a cyclic carbonate or a chain carbonate.

In some embodiments, the cyclic carbonate is one or more selected from ethylene carbonate, propylene carbonate, butylene carbonate, γ-butyrolactone, pentylene carbonate, fluoroethylene carbonate and their halogenated derivatives. The above cyclic carbonates may be used alone or in combination of two or more thereof.

In some embodiments, the chain carbonate is one or more selected from dimethyl carbonate, diethyl carbonate, dipropyl carbonate, ethyl methyl carbonate and their halogenated derivatives. The above chain carbonates may be used alone or in combination of two or more thereof.

In some embodiments, the electrolyte may further comprise other additives which are well known in the art for improving battery performance, such as solid electrolyte interface (SEI) film forming additives, flame retardant additives, anti-overcharge additives, conductive additives, etc.

II. Electrochemical Device

The electrochemical device of the present application includes any device in which an electrochemical reaction takes place, and specific examples include all kinds of primary batteries, secondary batteries, fuel cells, solar cells, or capacitors. In particular, the electrochemical device is a lithium secondary battery including a lithium metal secondary battery, a lithium ion secondary battery, a lithium polymer secondary battery or a lithium ion polymer secondary battery. In some embodiments, the electrochemical device of the present application is an electrochemical device having a cathode having a cathode active material capable of absorbing and releasing metal ions; an anode having an anode active material capable of absorbing and releasing metal ions, and characterized by comprising any of the electrolytes of the present application.

Electrolyte

The electrolyte used in the electrochemical device of the present application is any of the aforementioned electrolytes according to the present application. Moreover, the electrolyte used in the electrochemical device of the present application may include other electrolytes falling within the scope of the present application.

Anode

The anode material used in the electrochemical device of the present application, and the construction and manufacturing methods thereof are not particularly limited, and may be any of the techniques disclosed in the prior art. In some embodiments, the negative electrode may be one described in U.S. Pat. No. 9,812,739B, which is incorporated herein by reference in its entirety.

In some embodiments, the anode includes a current collector and an anode active material layer on the current collector. The anode active material includes a material that reversibly intercalates/deintercalates lithium ions. In some embodiments, the material that reversibly intercalates/deintercalates lithium ions includes a carbon material. In some embodiments, the carbon material may be any carbon-based anode active material commonly used in lithium ion rechargeable batteries. In some embodiments, the carbon material includes, but is not limited to, crystalline carbon, amorphous carbon, or a mixture thereof. The crystalline carbon may be formless or plate-shaped, platelet-shaped, spherical or fibrous natural graphite or artificial graphite. The amorphous carbon may be soft carbon, hard carbon, carbonized mesophase pitch, calcined coke, and the like.

In some embodiments, the anode active material layer comprises an anode active material. In some embodiments, the anode active material includes, but is not limited to, lithium metal, structured lithium metal, natural graphite, artificial graphite, mesocarbon microbead (MCMB), hard carbon, soft carbon, silicon, a silicon-carbon composite, a Li—Sn alloy, a Li—Sn—O alloy, Sn, SnO, $SnO_2$, lithiated $TiO_2$—$Li_4Ti_5O_{12}$ having a spinel structure, a Li—Al alloy and any combination thereof.

When the anode comprises a silicon-carbon compound, based on the total weight of the anode active material, the ratio of silicon to carbon is about 1:10 to about 10:1, and the median diameter D50 of the silicon-carbon compound is about 0.1 μm to about 100 μm. When the anode comprises an alloy material, an anode active material layer can be formed by vapor deposition, sputtering, or plating. When the anode comprises lithium metal, an anode active material layer is formed from, for example a conductive skeleton of a twisted spherical shape and metal particles dispersed in the conductive skeleton. In some embodiments, the conductive skeleton of a twisted spherical shape may have a porosity of about 5% to about 85%. In some embodiments, a protective layer may be further disposed on the negative electrode active material layer of lithium metal.

In some embodiments, the anode active material layer comprises a binder, and optionally a conductive material. The binder increases the binding of the anode active material particles to each other and the binding of the anode active material to the current collector. In some embodiments, the binder includes, but is not limited to, polyvinyl alcohol, carboxymethyl cellulose, hydroxypropyl cellulose, diacetyl cellulose, polyvinyl chloride, carboxylated polyvinyl chloride, polyvinyl fluoride, a polymer containing ethylene oxide, polyvinylpyrrolidone, polyurethane, polytetrafluoroethylene, poly(1,1-vinylidene fluoride), polyethylene, polypropylene, styrene butadiene rubber, acrylated styrene butadiene rubber, epoxy resins, nylon and so on.

In some embodiments, the conductive material includes, but is not limited to, a carbon based material, a metal based material, a conductive polymer, or a mixture thereof. In some embodiments, the carbon-based material is selected from natural graphite, artificial graphite, carbon black, acetylene black, Ketjen black, carbon fiber, or any combinations thereof. In some embodiments, the metal based material is selected from metal powders, metal fibers, copper, nickel, aluminum, and silver. In some embodiments, the conductive polymer is a polyphenylene derivative.

In some embodiments, the current collector includes, but is not limited to, copper foil, nickel foil, stainless steel foil, titanium foil, foamed nickel, foamed copper, polymeric substrates coated with a conductive metal, and any combinations thereof.

The anode can be produced by a production method well known in the art. For example, the anode can be obtained by mixing an active material, a conductive material and a binder in a solvent to prepare an active material composition, and coating the active material composition on a current collector. In some embodiments, the solvent may include, but is not limited to, water.

Cathode The cathode material used in the electrochemical device of the present application can be prepared using materials, construction and manufacturing methods well known in the art. In some embodiments, the cathode of the present application can be prepared using the technique described in U.S. Pat. No. 9,812,739B2, which is incorporated herein by reference in its entirety.

In some embodiments, the cathode includes a current collector and a cathode active material layer on the current collector. The cathode active material includes at least one lithiated intercalation compound that reversibly intercalates and deintercalates lithium ions. In some embodiments, the cathode active material comprises a composite oxide. In some embodiments, the composite oxide contains lithium and at least one element selected from the group consisting of cobalt, manganese, and nickel.

In some embodiments, the cathode active material is selected from lithium cobalt oxide ($LiCoO_2$), lithium nickel cobalt manganese (NCM) ternary material, lithium iron phosphate ($LiFePO_4$), lithium manganate ($LiMn_2O_4$) or any combinations thereof.

In some embodiments, the cathode active material may have a coating on its surface or may be mixed with another compound having a coating. The coating may include at least one coating element compound selected from the group consisting of an oxide of a coating element, a hydroxide of a coating element, an oxyhydroxide of a coating element, an oxycarbonate of a coating element, and a hydroxycarbonate of a coating element. The compound used for the coating may be amorphous or crystalline.

In some embodiments, the coating element contained in the coating may include Mg, Al, Co, K, Na, Ca, Si, Ti, V, Sn, Ge, Ga, B, As, Zr or any combinations thereof. The coating can be applied by any method as long as the method does not adversely affect the performance of the positive electrode active material. For example, the method may include any coating method known in the art, such as spraying, dipping, and others.

The cathode active material layer further comprises a binder, and optionally a conductive material. The binder increases the binding of the cathode active material particles to each other and the binding of the cathode active material to the current collector.

In some embodiments, the binder includes, but is not limited to, polyvinyl alcohol, hydroxypropyl cellulose, diacetyl cellulose, polyvinyl chloride, carboxylated polyvinyl chloride, polyvinyl fluoride, a polymer containing ethylene oxide, polyvinylpyrrolidone, polyurethane, polytetrafluoroethylene, poly(1,1-vinylidene fluoride), polyethylene, polypropylene, styrene butadiene rubber, acrylated styrene butadiene rubber, epoxy resins, nylon and so on.

In some embodiments, the conductive material includes, but is not limited to, a carbon based material, a metal based material, a conductive polymer, and a mixture thereof. In some embodiments, the carbon-based material is selected from natural graphite, artificial graphite, carbon black, acetylene black, Ketjen black, carbon fiber, or any combinations thereof. In some embodiments, the metal based material is selected from metal powders, metal fibers, copper, nickel, aluminum, and silver. In some embodiments, the conductive polymer is a polyphenylene derivative.

In some embodiments, the current collector may be, but is not limited to, aluminum.

The cathode can be prepared by a preparation method well known in the art. For example, the cathode can be obtained by mixing an active material, a conductive material and a binder in a solvent to prepare an active material composition, and coating the active material composition on a current collector. In some embodiments, the solvent may include, but is not limited to, N-methylpyrrolidone or the like.

In some embodiments, the positive electrode is prepared by forming a cathode material with a cathode active material layer including a lithium-transition metal compound powder and a binder on a current collector.

In some embodiments, the positive electrode active material layer can generally be produced by dry mixing a cathode material and a binder (and a conductive material and a thickener if needed) to form flakes, and pressing the obtained flakes on a cathode current collector; or dissolving or dispersing the material in a liquid medium to form a slurry, coating the slurry on a cathode current collector, and drying. In some embodiments, the material of the cathode active material layer includes any material known in the art.

Separator

In some embodiments, the electrochemical device of the present application is provided with a separator between the cathode and the anode to prevent short circuit. The material and shape of the separator used in the electrochemical device of the present application are not particularly limited, and may be any of the techniques disclosed in the prior art. In some embodiments, the separator includes a polymer or an inorganic substance or the like formed of a material which is stable against the electrolyte of the present application.

For example, the separator may include a substrate layer and a surface treatment layer. The substrate layer is a non-woven fabric, film, or composite film having a porous structure, and the material of the substrate layer is at least one selected from the group consisting of polyethylene, polypropylene, polyethylene terephthalate, and polyimide. Particularly, a porous polypropylene film, a porous polyethylene film, a polypropylene nonwoven fabric, a polyethylene nonwoven fabric, and a porous polypropylene-polyethylene-polypropylene composite film may be used.

At least one surface of the substrate layer is provided with a surface treatment layer, which may be a polymer layer or an inorganic layer, or a layer formed by mixing a polymer and an inorganic material.

The inorganic layer comprises inorganic particles and a binder. The inorganic particles are at least one selected from the group consisting of alumina, silica, magnesia, titania, hafnium dioxide, tin oxide, cerium dioxide, nickel oxide, zinc oxide, calcium oxide, zirconia, yttria, silicon carbide, eboehmite, aluminum hydroxide, magnesium hydroxide, calcium hydroxide and barium sulfate, or a combination of more than one thereof. The binder is one selected from the group consisting of polyvinylidene fluoride, a copolymer of vinylidene fluoride-hexafluoropropylene, a polyamide, polyacrylonitrile, a polyacrylate ester, polyacrylic acid, a polyacrylate salt, polyvinylpyrrolidone, polyvinyl ether, polymethyl methacrylate, polytetrafluoroethylene, and polyhexafluoropropylene, or a combination of more than one thereof. The polymer layer contains a polymer, and the material of the polymer includes at least one of a polyamide, polyacrylonitrile, a polyacrylate ester, polyacrylic acid, a polyacrylate salt, polyvinylpyrrolidone, polyvinyl ether, polyvinylidene fluoride or poly(vinylidene fluoride-hexafluoropropylene).

III. Application

The electrolyte according to the embodiments of the present application can be used to enhance the rate performance of the battery, the capacity retention rate upon storage at normal temperature, and the cycle and high-temperature storage performance and is thus applicable to an electronic device comprising an electrochemical device.

The use of the electrochemical device according to the present application is not particularly limited, and can be used in various known applications, such as notebook computers, pen-input computers, mobile computers, e-book players, portable phones, portable fax machines, portable copiers, portable printers, head-mounted stereo headphones, video recorders, LCD TVs, portable cleaners, portable CD players, mini disc players, transceivers, electronic notebooks, calculators, memory cards, portable recorders, radios, backup power sources, motors, vehicles, motorcycles, scooters, bicycles, lighting apparatuses, toys, game consoles, clocks, electric tools, flash lights, cameras, large batteries for household use, or lithium ion capacitors.

Examples

Hereinafter, the present application will be specifically described by way of examples and comparative examples; however, the present application is not limited thereto as long as they do not deviate from the spirit of the present application.

Preparation of Lithium-Ion Battery (1) Preparation of a Cathode

The cathode active material lithium cobalt oxide (LiCoO$_2$), the conductive agent (Super P® conductive carbon), and polyvinylidene fluoride were mixed at a weight ratio of 97:1.4:1.6, and N-methylpyrrolidone (NMP) was added and stirred in a vacuum mixer, until the material became homogeneous to obtain a cathode slurry. The cathode slurry had a solid content of 72 wt %. The cathode slurry was uniformly coated on an aluminum foil which was a cathode current collector, dried at 85° C., cold pressed, cut, sliced, and dried under vacuum at 85° C. for 4 h to obtain the cathode.

(2) Preparation of an Anode

The anode active material artificial graphite, the conductive agent (Super P® conductive carbon), sodium carboxymethylcellulose (CMC), and the binder styrene-butadiene rubber (SBR) were mixed at a weight ratio of 96.4:1.5:0.5:1.6, and deionized water was added and stirred in a vacuum mixer, to obtain an anode slurry. The anode slurry had a solid content of 54 wt %. The anode slurry was uniformly coated on a copper foil which was an anode current collector, dried at 85° C., cold pressed, cut, sliced, and dried under vacuum at 120° C. for 12 h to obtain the anode.

(3) Preparation of Electrolyte

In a dry argon atmosphere glovebox, a solvent (such as ethylene carbonate (EC), propylene carbonate (PC), diethyl carbonate (DEC), ethyl acetate (EA), methyl propionate (MP), and ethyl propionate (EP)) were mixed at a certain weight ratio. An additive (such as a barbituric acid compound, a nitrile compound, or a carbonate compound containing a silicon functional group) was added, dissolved and fully stirred, and then the lithium salt LiPF$_6$ was added and mixed uniformly to obtain an electrolyte. The concentration of LiPF$_6$ was 1.05 mol/L. The contents of each substance in the electrolyte were calculated based on the total weight of the electrolyte.

(4) Preparation of Separator

A 12 μm thick polyethylene (PE) separator was used.

(5) Preparation of Lithium-Ion Battery

The cathode, the separator, and the anode were stacked in sequence, where the separator was placed between the cathode and anode so as to separate the cathode and the anode, then wound up, a tab was welded, and was placed in the outer packaging foil which was an aluminum plastic film. The electrolyte prepared above was injected into a dry bare battery cell, and after vacuum packaging, standing, formation (by charging to 3.3 V at a constant current of 0.02 C, and then charging to 3.6 V at a constant current of 0.1 C), shaping, capacity testing, and other procedures, a soft-package lithium ion battery (having a thickness of 3.3 mm, a width of 39 mm, and a length of 96 mm) was obtained.

A. Electrolytes and lithium ion batteries of Examples 1-30 and Comparative Examples 1-14 were prepared as described above.

TABLE 1

| | Solvent | Barbituric acid compound | | Nitrile compound | |
|---|---|---|---|---|---|
| | | Structure of compound | Content (wt %) | Structure of compound | Content (wt %) |
| Comparative Example 1 | EC:PC:DEC = 20:20:60 | — | — | — | — |
| Comparative Example 2 | EC:PC:DEC:EA = 20:20:30:30 | — | — | — | — |
| Comparative Example 3 | EC:PC:DEC:EA = 20:20:30:30 | Compound 1-1 | 1 | — | — |
| Comparative Example 4 | EC:PC:DEC:EA = 20:20:30:30 | Compound 1-2 | 1 | — | — |
| Comparative Example 5 | EC:PC:DEC:EA = 20:20:30:30 | Compound 1-13 | 1 | — | — |
| Comparative Example 6 | EC:PC:DEC:EA = 20:20:30:30 | — | — | Compound 2-2 | 3 |
| Comparative Example 7 | EC:PC:DEC:EA = 20:20:30:30 | — | — | Compound 2-7 | 2 |
| Comparative Example 8 | EC:PC:DEC:EA = 8:20:50 PM:10 | — | — | — | — |
| Comparative Example 9 | EC:PC:DEC:EA = 8:20:10 PM:50 | — | — | — | — |
| Comparative Example 10 | EC:PC:EA = 20:20:60 | — | — | — | — |
| Comparative Example 11 | EC:PC:DEC:MA = 20:20:30:30 | Compound 1-1 | 1 | — | — |
| Comparative Example 12 | EC:PC:DEC:MP = 20:20:30:30 | Compound 1-1 | 1 | — | — |
| Comparative Example 13 | EC:PC:DEC:EP = 20:20:30:30 | Compound 1-1 | 1 | — | — |
| Comparative Example 14 | EC:PC:DEC:PP = 20:20:30:30 | Compound 1-1 | 1 | — | — |
| Example 1 | EC:PC:DEC:EA = 20:20:30:30 | Compound 1-1 | 1 | Compound 2-2 | 3 |
| Example 2 | EC:PC:DEC:EA = 20:20:30:30 | Compound 1-1 | 1 | Compound 2-7 | 2 |
| Example 3 | EC:PC:DEC:EA = 20:20:30:30 | Compound 1-1 | 0.01 | Compound 2-7 | 2 |
| Example 4 | EC:PC:DEC:EA = 20:20:30:30 | Compound 1-1 | 0.1 | Compound 2-7 | 2 |
| Example 5 | EC:PC:DEC:EA = 20:20:30:30 | Compound 1-1 | 0.5 | Compound 2-7 | 2 |
| Example 6 | EC:PC:DEC:EA = 20:20:30:30 | Compound 1-1 | 2 | Compound 2-7 | 2 |
| Example 7 | EC:PC:DEC:EA = 20:20:30:30 | Compound 1-1 | 3 | Compound 2-7 | 2 |
| Example 8 | EC:PC:DEC:EA = 20:20:30:30 | Compound 1-1 | 4 | Compound 2-7 | 2 |
| Example 9 | EC:PC:DEC:EA = 20:20:30:30 | Compound 1-1 | 5 | Compound 2-7 | 2 |
| Example 10 | EC:PC:DEC:EA = 20:20:30:30 | Compound 1-1 | 1 | Compound 2-7 | 0.5 |
| Example 11 | EC:PC:DEC:EA = 20:20:30:30 | Compound 1-1 | 1 | Compound 2-7 | 1 |
| Example 12 | EC:PC:DEC:EA = 20:20:30:30 | Compound 1-1 | 1 | Compound 2-7 | 1.5 |
| Example 13 | EC:PC:DEC:EA = 20:20:30:30 | Compound 1-1 | 1 | Compound 2-7 | 2.5 |
| Example 14 | EC:PC:DEC:EA = 20:20:30:30 | Compound 1-1 | 1 | Compound 2-7 | 3 |
| Example 15 | EC:PC:DEC:EA = 20:20:30:30 | Compound 1-1 | 1 | Compound 2-7 | 5 |
| Example 16 | EC:PC:DEC:EA = 20:20:30:30 | Compound 1-1 | 1 | Compound 2-7; Compound 2-2 | 2; 3 |
| Example 17 | EC:PC:DEC:EA = 20:20:30:30 | Compound 1-1 | 1 | Compound 2-7; Compound 2-2 | 2; 5 |
| Example 18 | EC:PC:DEC:EA = 20:20:30:30 | Compound 1-1 | 1 | Compound 2-7; Compound 2-2; Compound 2-3 | 2; 3; 3 |
| Example 19 | EC:PC:DEC:EA = 20:20:30:30 | Compound 1-1 | 1 | Compound 2-7; Compound 2-2; Compound 2-3 | 2; 4; 6 |
| Example 20 | EC:PC:DEC:EA = 20:20:30:30 | Compound 1-1 | 1 | Compound 2-5 | 2 |
| Example 21 | EC:PC:DEC:EA = 20:20:30:30 | Compound 1-1 | 1 | Compound 2-5; Compound 2-2 | 2; 3 |
| Example 22 | EC:PC:DEC:EA = 20:20:30:30 | Compound 1-1 | 1 | Compound 2-6 | 2 |

TABLE 1-continued

|  | Solvent | Barbituric acid compound | | Nitrile compound | |
|---|---|---|---|---|---|
|  |  | Structure of compound | Content (wt %) | Structure of compound | Content (wt %) |
| Example 23 | EC:PC:DEC:EA = 20:20:30:30 | Compound 1-1 | 1 | Compound 2-4 | 2 |
| Example 24 | EC:PC:DEC:EA = 20:20:30:30 | Compound 1-2 | 1 | Compound 2-7 | 2 |
| Example 25 | EC:PC:DEC:EA = 20:20:30:30 | Compound 1-13 | 1 | Compound 2-7 | 2 |
| Example 26 | EC:PC:DEC:EA = 20:20:30:30 | Compound 1-10 | 1 | Compound 2-7 | 2 |
| Example 27 | EC:PC:DEC:MA = 20:20:30:30 | Compound 1-1 | 1 | Compound 2-7 | 2 |
| Example 28 | EC:PC:DEC:MP = 20:20:30:30 | Compound 1-1 | 1 | Compound 2-7 | 2 |
| Example 29 | EC:PC:DEC:EP = 20:20:30:30 | Compound 1-1 | 1 | Compound 2-7 | 2 |
| Example 30 | EC:PC:DEC:PP = 20:20:30:30 | Compound 1-1 | 1 | Compound 2-7 | 2 |

"—"denotes that the substance is not present.

The high-temperature cycle performance, high-temperature storage performance and 2 C discharge efficiency of the lithium ion batteries of Examples 1-30 and Comparative Examples 1-14 were tested. The test process was as follows:

(1) High-Rate Discharge Performance Test of Lithium-Ion Batteries

The lithium ion batteries obtained in Comparative Examples 1-14 and Examples 1-30 were charged to 4.4 V at a constant current/constant voltage of 0.5 C at 25° C., allowed to stand for 10 min, and discharged at a constant current of 0.5 C to a cutoff voltage of 3.0 V, and the discharge capacity was recorded. The lithium ion batteries were charged to 4.4 V at a constant current/constant voltage of 0.5 C at 25° C., allowed to stand for 10 min, and discharged at a constant current of 2 C to a cutoff voltage of 3.0 V, and the discharge capacity was recorded. The ratio of this discharge capacity to the 0.5 C capacity at 25° C. is the 2 C discharge efficiency. Table 2 shows the 2 C discharge performance test data of the lithium batteries of Comparative Examples 1-14 and Examples 1-30.

(2) Capacity Retention Test of the Lithium-Ion Batteries after Storage at Room Temperature The lithium ion batteries were placed in an incubator at 25° C. and allowed to stand for 30 minutes to allow the lithium ion battery to reach a constant temperature. The lithium ion battery reaching a constant temperature was charged at a constant current of 1 C to a voltage of 4.4 V and then charged at a constant voltage of 4.4 V until the current was 0.05 C, and then discharged at a constant current of 1 C to a voltage of 3.0 V. This capacity was the initial capacity. Then, the lithium ion battery was charged to 3.85 V at a constant current of 1 C and then charged to a current of 0.05 C (about 50% State of Charge (SOC)) at a constant voltage of 3.85 V, stored at 25° C. for 6 months, discharged to a voltage of 3.0 V at a constant current of 1 C, charged to a voltage of 4.4 V at a constant current of 1 C and then charged to a current of 0.05 C at a constant voltage of 4.4 V, and then discharged to a voltage of 3.0 V at a constant current of 1 C. The last discharge capacity is called post-storage reversible capacity.

The capacity retention rate (%) of the lithium ion battery after storage at room temperature=post-storage reversible capacity/initial capacity×100%

(3) Cycle Performance Test of the Lithium Ion Batteries

The lithium ion batteries were placed in an incubator at 45° C. and allowed to stand for 30 minutes to allow the lithium ion battery to reach a constant temperature. The lithium ion battery reaching a constant temperature was charged to a voltage of 4.4 V at a constant current of 1 C, then charged at a constant voltage of 4.4 V until the current was 0.05 C, and then discharged to a voltage of 3.0 V at a constant current of 1 C. The above was one charge-discharge cycle. Repeating charging/discharging as described above, the capacity retention rates of the battery after 300 and 500 cycles were calculated respectively. Table 2 shows the cycle test data at 45° C. of the lithium ion batteries of Comparative Examples 1-14 and Examples 1-30.

Capacity Retention Rate (%) of the Lithium Ion Battery after $N$ Cycles=Discharge Capacity after the $N$th Cycle/the First Discharge Capacity×100%.

(4) High-Temperature Storage Performance Test of the Lithium Ion Batteries

The lithium ion batteries obtained in Comparative Examples 1-14 and Examples 1-30 were charged to 4.4 V at a constant current of 0.5 C at room temperature and then charged to a current of 0.05 C at a constant voltage, and the thickness of the lithium ion battery was measured and recorded as h0. Then, the lithium ion battery was placed in an incubator at 60° C. for 30 days, and the thickness of the lithium ion battery was tested every 10 days and recorded as hn, where n was the number of days after high temperature storage of the lithium ion battery. Table 2 shows the storage test data at 60° C. of the lithium ion batteries of Comparative Examples 1-14 and Examples 1-30.

Thickness expansion rate (%) of lithium ion battery after $n$ days of high temperature storage= $(hn-h0)/h0\times100\%$

TABLE 2

| | 2 C discharge efficiency (%) | Capacity retention rate after n cycles at 45° C. | | Capacity retention rate after storage at room temperature | Thickness expansion rate after n days of storage at 60° C. | | |
|---|---|---|---|---|---|---|---|
| | | 200th | 300th | 6 months | 10 d | 20 d | 30 d |
| Comparative Example 1 | 45.4 | 86.6 | 62.5 | 90.20% | 5.9 | 15.4 | 20.3 |
| Comparative Example 2 | 80.1 | 80.5 | 54.3 | 80.40% | 11.1 | 29.9 | 45.2 |
| Comparative Example 3 | 80 | 88.9 | 68.3 | 83.90% | 7.3 | 19.9 | 23.8 |
| Comparative Example 4 | 79.9 | 88.5 | 67.9 | 83.50% | 8 | 21 | 26.1 |
| Comparative Example 5 | 79.8 | 88.3 | 67.2 | 83.20% | 7.5 | 20.4 | 24.3 |
| Comparative Example 6 | 78.5 | 87.4 | 64.5 | 86.10% | 5.6 | 14.5 | 18.9 |
| Comparative Example 7 | 78.7 | 88.2 | 66.6 | 86.80% | 5.3 | 13.9 | 17.8 |
| Comparative Example 8 | 56.4 | 84.5 | 59.7 | 88.60% | 8.7 | 18.9 | 25.1 |
| Comparative Example 9 | 92.9 | 74.5 | 39.4 | 75.10% | 18.2 | 35.6 | 60.9 |
| Comparative Example 10 | 98.2 | 57.2 | 28.1 | 71.80% | 23.1 | 44.7 | 79.8 |
| Comparative Example 11 | 87.7 | 86.3 | 59.6 | 79.9% | 10.5 | 23.4 | 34.6 |
| Comparative Example 12 | 75.0 | 89.2 | 68.7 | 84.2% | 7.1 | 19.0 | 22.9 |
| Comparative Example 13 | 69.4 | 89.3 | 68.9 | 89.6 | 6.2 | 17.8 | 21.1 |
| Comparative Example 14 | 55.3 | 89.5 | 69.2 | 90.1% | 5.9 | 15.6 | 20.3 |
| Example 1 | 78.6 | 92.2 | 78.3 | 90.50% | 5.2 | 13.2 | 17.3 |
| Example 2 | 78.5 | 92.5 | 80.2 | 92.50% | 3.3 | 6.1 | 10.1 |
| Example 3 | 78.8 | 89.8 | 69.9 | 90.60% | 5.2 | 10.5 | 16.8 |
| Example 4 | 78.7 | 90.9 | 71.4 | 90.80% | 5.1 | 9.8 | 15.9 |
| Example 5 | 78.9 | 92.1 | 73.6 | 91.20% | 4.1 | 8.7 | 14.2 |
| Example 6 | 78.1 | 91.8 | 76.8 | 91.70% | 3.5 | 6.1 | 9.5 |
| Example 7 | 77.9 | 90.5 | 73.2 | 91.50% | 3.2 | 5.4 | 8.3 |
| Example 8 | 77.2 | 89.8 | 70.1 | 91.40% | 3.1 | 5.3 | 7.9 |
| Example 9 | 76.8 | 90.5 | 69.7 | 91.10% | 3.1 | 5 | 7.3 |
| Example 10 | 79.2 | 90.8 | 71.3 | 90.90% | 5.1 | 9.7 | 15.2 |
| Example 11 | 79 | 91.5 | 73.6 | 91.20% | 4.2 | 8.6 | 13.8 |
| Example 12 | 78.8 | 91.9 | 76.8 | 91.90% | 3.8 | 7.5 | 11.9 |
| Example 13 | 78.3 | 92.4 | 79.9 | 92.60% | 3.2 | 5.9 | 8.5 |
| Example 14 | 77.9 | 91.8 | 76.7 | 92.30% | 3 | 5.1 | 7.1 |
| Example 15 | 76.7 | 90.6 | 72.2 | 92.20% | 3 | 4.5 | 5.9 |
| Example 16 | 78.2 | 92.6 | 79.9 | 92.70% | 3.2 | 5.3 | 7.7 |
| Example 17 | 77.9 | 91.7 | 76.5 | 92.30% | 2.9 | 4.8 | 6.9 |
| Example 18 | 77.2 | 90.6 | 73.3 | 92.40% | 2.8 | 4.7 | 5.8 |
| Example 19 | 77.0 | 90.2 | 71.3 | 92.40% | 2.8 | 4.5 | 5.3 |
| Example 20 | 78.5 | 92.1 | 79.9 | 92.30% | 3.4 | 6.9 | 10.8 |
| Example 21 | 78.3 | 92.3 | 80 | 92.40% | 3.3 | 5.7 | 8.1 |
| Example 22 | 78.8 | 92.4 | 80.1 | 92.50% | 3.4 | 6.3 | 10.4 |
| Example 23 | 78.6 | 92.2 | 78.4 | 90.80% | 5.1 | 11.5 | 16.8 |
| Example 24 | 78.4 | 92.3 | 79.8 | 92.20% | 3.4 | 6.5 | 10.9 |
| Example 25 | 78.3 | 91.2 | 78.3 | 91.30% | 3.6 | 7.2 | 11.4 |
| Example 26 | 78.2 | 91.3 | 78.5 | 91.60% | 3.5 | 7 | 11.1 |
| Example 27 | 87.4 | 91.8 | 72.5 | 91.10% | 5.2 | 8.8 | 15.3 |
| Example 28 | 74.9 | 93.3 | 82.9 | 93.50% | 3.2 | 5.6 | 9.1 |
| Example 29 | 69.3 | 93.8 | 84.1 | 95.60% | 3 | 5.2 | 7.9 |
| Example 30 | 54.5 | 95.6 | 85.3 | 96.50% | 2.9 | 5 | 7.1 |

From the test results of Comparative Examples 1-7 and Examples 1-26, it can be seen that adding a barbituric acid compound and a nitrile compound of a particular structure to the carboxylate-containing electrolyte significantly improves the rate performance of the lithium ion battery and improves the irreversible capacity loss after storage at room temperature, as well as the cycle performance and high-temperature storage performance.

From the test results of Comparative Examples 2, 3 and 7 and Examples 2 and 10-23, it can be seen that when the electrolyte contains 1 wt % of a barbituric acid compound and 0.5-12 wt % of a particular nitrile compound simultaneously, the capacity loss after storage at room temperature and the high-temperature storage performance of the battery can be improved. From the test results of Comparative Examples 2, 3 and 7 and Examples 2-9, it can be seen that when the electrolyte contains 2 wt % of a nitrile compound and 0.01-5 wt % of a barbituric acid compound simultaneously, the capacity loss after storage at room temperature and the high-temperature storage performance of the battery can be improved. The above test results show that when the electrolyte contains a carboxylate, a barbituric acid compound and a nitrile compound of particular structure simultaneously, the large-rate performance of the battery can be effectively improved, and the problems of irreversible capacity loss after storage at room temperature, cycle fading and gas generation at high-temperature of the lithium ion batteries can be effectively improved.

B. The electrolytes of Examples 31-40 were prepared by adding a carbonate compound containing a silicon functional group to the electrolyte of Example 2.

The capacity retention rate and overcharge performance of the batteries of Examples 2 and 31-40 at room temperature storage were tested. The test results are shown in Table 2.

The overcharge performance test process was as follows. The battery was discharged at 0.5 C to 2.8 V at 25° C., charged to 5 V at a constant current of 2 C, and then charged for 3 h at a constant voltage. If the battery did not burn or explode, the battery passed the test.

TABLE 2

|  | Carbonate compound containing silicon functional group (wt %) | | | Capacity retention rate after storage at room temperature (%) | Overcharge test |
| --- | --- | --- | --- | --- | --- |
|  | Compound 3-1 | Compound 3-2 | Compound 3-3 | | |
| Example 2 | — | — | — | 92.5% | 0/10 pass |
| Example 31 | 1 | — | — | 92.7% | 2/10 pass |
| Example 32 | 5 | — | — | 93.0% | 5/10 pass |
| Example 33 | 7 | — | — | 93.2% | 7/10 pass |
| Example 34 | 10 | — | — | 93.4% | 8/10 pass |
| Example 35 | 12 | — | — | 93.3% | 9/10 pass |
| Example 36 | 15 | — | — | 92.9% | 10/10 pass |
| Example 37 | 30 | — | — | 92.6% | 10/10 pass |
| Example 38 | — | 5 | — | 93.1% | 5/10 pass |
| Example 39 | — | 10 | — | 92.8% | 8/10 pass |
| Example 40 | — | — | 5 | 93.0% | 5/10 pass |

"—"denotes that the substance is not present.

It can be seen from the test results of Examples 31-40 and Example 2 that adding a carbonate compound containing a silicon functional group to an electrolyte containing a barbituric acid compound and a nitrile compound can improve the capacity retention rate of the battery after storage at room temperature, and greatly improve the overcharge performance of the battery.

Several embodiments have been illustrated above, and the present invention is not limited thereto in any way. Although the present invention has been described through preferred embodiments, they are not intended to limit the scope of the present invention. It should be understood by any person of skill in the art that changes and modifications made to the technical contents disclosed above without departing from the scope of the technical solution of the present invention are equivalent implementations, and are all contemplated in the protection scope of the present invention.

References throughout the specification to "some embodiments", "partial embodiments", "one embodiment", "another example", "example", "specific example" or "partial examples" mean that at least one embodiment or example of the application includes specific features, structures, materials or characteristics described in the embodiments or examples. Thus, the descriptions appear throughout the specification, such as "in some embodiments", "in an embodiment", "in one embodiment", "in another example", "in an example", "in a particular example" or "for example", are not necessarily the same embodiment or example in the application. Furthermore, the particular features, structures, materials or characteristics herein may be combined in any suitable manner in one or more embodiments or examples.

While the illustrative embodiments have been shown and described, it will be understood by those skilled in the art that the embodiments are not to be construed as limiting the present invention, and modifications, substitutions and changes can be made to the embodiments without departing from the spirit and scope of the present application.

The above-described embodiments of the present invention are intended to be illustrative only. Numerous alternative embodiments may be devised by persons skilled in the art without departing from the scope of the following claims.

What is claimed is:

1. An electrolyte, comprising a carboxylate, a barbituric acid compound, a carbonate compound containing a silicon functional group and a nitrile compound;

wherein, the nitrile compound comprises one or more selected from the group consisting of

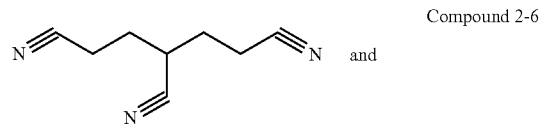

Compound 2-6

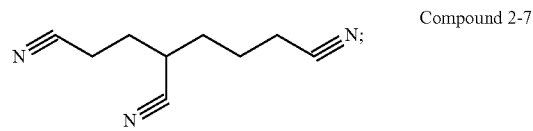

Compound 2-7 and wherein, the carbonate compound containing a silicon-functional group comprises one or more selected from the group consisting of

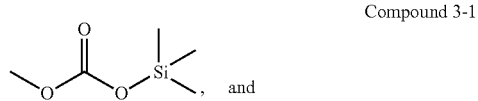

Compound 3-1 and

Compound 3-3

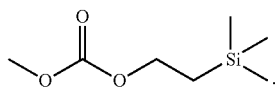

2. The electrolyte according to claim 1, wherein the carboxylate comprises at least one of the compounds of Formula 1:

Formula 1

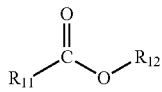

where $R_{11}$ and $R_{12}$ are each independently selected from $C_{1-12}$alkyl or $C_{1-12}$halogenated alkyl.

3. The electrolyte according to claim 1, wherein the carboxylate comprises one or more of:
methyl acetate, ethyl acetate, propyl acetate, methyl propionate, ethyl propionate and propyl propionate.

4. The electrolyte according to claim 1, wherein the content of the carboxylate is about 5 wt % to about 70 wt % based on the total weight of the electrolyte.

5. The electrolyte according to claim 1, wherein the barbituric acid compound comprises at least one of the compounds of Formula 2:

Formula 2

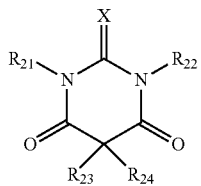

where $R_{21}$ and $R_{22}$ are each independently selected from hydrogen, $C_1$-$C_{12}$alkyl, $C_1$-$C_{12}$halogenated alkyl, $C_2$-$C_{12}$ alkenyl, $C_2$-$C_{12}$halogenated alkenyl, $C_6$-$C_{26}$aryl or $C_6$-$C_{26}$halogenated aryl;

$R_{23}$ and $R_{24}$ are each independently selected from hydrogen, amino, $C_1$-$C_{12}$alkyl, $C_1$-$C_{12}$halogenated alkyl, $C_2$-$C_{12}$alkenyl, $C_2$-$C_{12}$halogenated alkenyl, $C_6$-$C_{26}$aryl, $C_6$-$C_{26}$halogenated aryl or —NH—R', in which R' is $C_1$-$C_{12}$alkyl or $C_1$-$C_{12}$halogenated alkyl; and X is selected from O or S.

6. The electrolyte according to claim 1, wherein the barbituric acid compound comprises one or more of:

Compound 1-1

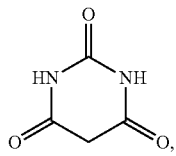

Compound 1-2

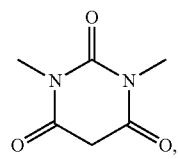

Compound 1-3

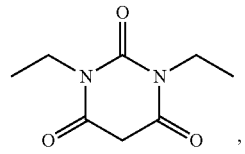

Compound 1-4

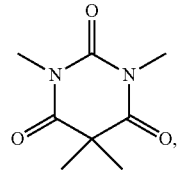

Compound 1-5

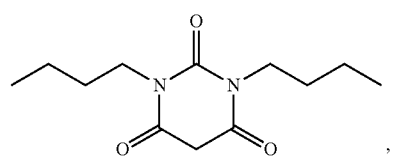

Compound 1-6

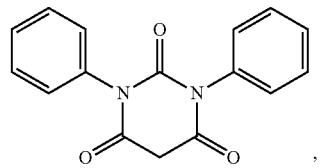

Compound 1-7

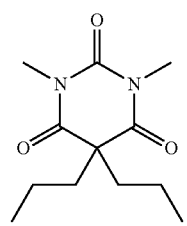

Compound 1-8

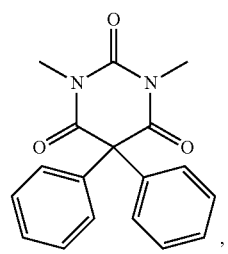

Compound 1-9

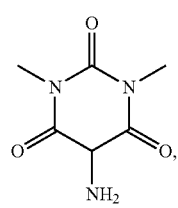

-continued

Compound 1-10
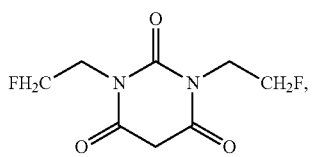

Compound 1-11
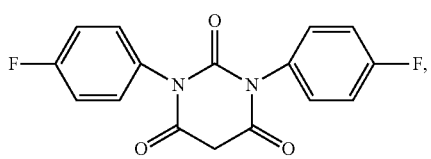

Compound 1-12
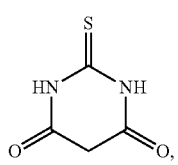

Compound 1-13
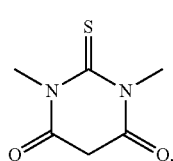

Compound 1-14
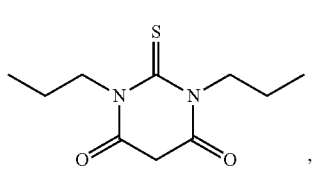

Compound 1-15
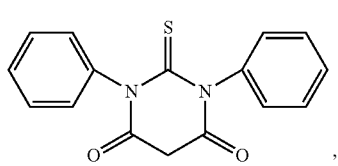

Compound 1-16
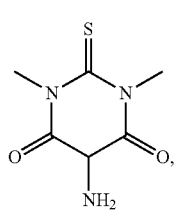

Compound 1-17
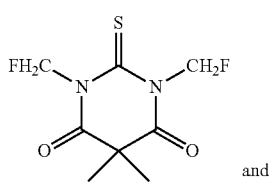
and

-continued

Compound 1-18
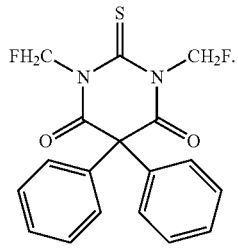

7. The electrolyte according to claim 1, wherein the content of the barbituric acid compound is about 0.01 wt % to about 5 wt % based on the total weight of the electrolyte.

8. The electrolyte according to claim 1, wherein the nitrile compound further comprises one or more selected from the group consisting of $$NC-R_{31}-CN, \quad \text{and} \qquad \text{Formula 3}$$

$$NC-R_{41}-\underset{H}{C}=\underset{H}{C}-R_{42}-NC; \qquad \text{Formula 4}$$

wherein $R_{31}$ is selected from $C_1$-$C_{12}$alkylene or $C_1$-$C_{12}$alkyleneoxy; and
$R_{41}$, and $R_{42}$ are each independently selected from a bond or $C_1$-$C_{12}$alkylene.

9. The electrolyte according to claim 1, wherein the nitrile compound further comprises one or more selected from the group consisting of Compound 2-1
NC–CH₂CH₂–CN, Compound 2-2
NC–(CH₂)₄–CN, Compound 2-3
NC–CH₂CH₂–O–CH₂CH₂–O–CH₂CH₂–CN, Compound 2-4
NC–CH=CH–CN.

10. The electrolyte according to claim 1, wherein the content of the nitrile compound is about 0.5 wt % to about 12 wt % based on the total weight of the electrolyte.

11. The electrolyte according to claim 1, wherein the carbonate compound containing the silicon-functional group comprises Compound 3-2
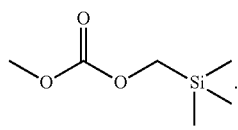

12. The electrolyte according to claim 1, wherein a content of the carbonate compound containing the silicon-functional group is about 1 wt % to about 30 wt % based on the total weight of the electrolyte.

13. An electrochemical device, comprising an electrolyte, wherein the electrolyte comprises a carboxylate, a barbituric acid compound, a carbonate compound containing a silicon functional group and a nitrile compound;

wherein, the nitrile compound comprises one or more selected from the group consisting of

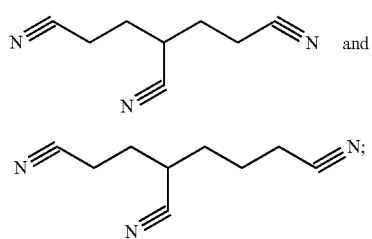

Compound 2-6 and

Compound 2-7 and wherein, the carbonate compound containing the silicon-functional group comprises one or more selected from the group consisting of

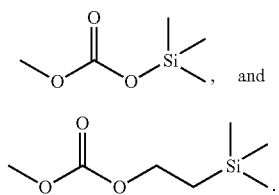

Compound 3-1 and

Compound 3-3

14. An electronic device, comprising an electrochemical device, wherein the electrochemical device comprises an electrolyte, wherein the electrolyte comprises a carboxylate, a barbituric acid compound, a carbonate compound containing a silicon functional group and a nitrile compound;

wherein, the nitrile compound comprises one or more selected from the group consisting of

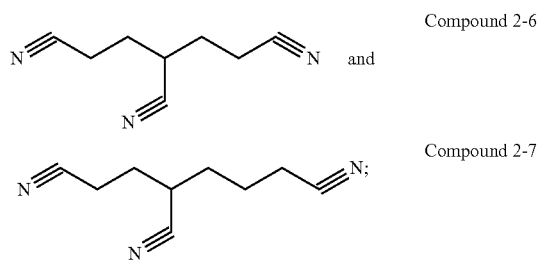

Compound 2-6 and

Compound 2-7 and wherein, the carbonate compound containing a silicon-functional group comprises one or more selected from the group consisting of

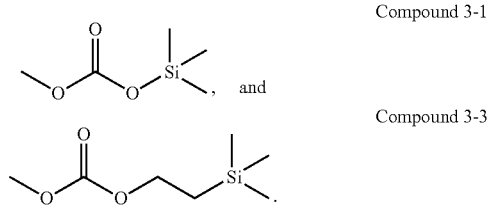

Compound 3-1 and

Compound 3-3

* * * * *